(12) United States Patent
Fukuyama et al.

(10) Patent No.: US 7,114,394 B2
(45) Date of Patent: Oct. 3, 2006

(54) VIBRATION TEST SYSTEM AND METHOD FOR STRUCTURES

(75) Inventors: Mayumi Fukuyama, Tokyo (JP); Takao Konno, Tokyo (JP); Kazuhiro Umekita, Tokyo (JP); Yoshihiro Dozono, Tokyo (JP); Toshihiko Horiuchi, Tokyo (JP); Michiya Sakai, Tokyo (JP); Yutaka Hagiwara, Tokyo (JP); Keizo Ohtomo, Tokyo (JP)

(73) Assignees: Hitachi Plant Technologies, Ltd., Tokyo (JP); Central Research Institute of Electric Power Industry, Tokyo (JP)

( * ) Notice: Subject to any disclaimer, the term of this patent is extended or adjusted under 35 U.S.C. 154(b) by 32 days.

(21) Appl. No.: 11/022,675

(22) Filed: Dec. 28, 2004

(65) Prior Publication Data

US 2005/0155431 A1    Jul. 21, 2005

(30) Foreign Application Priority Data

Jan. 19, 2004    (JP)    ............................. 2004-010047

(51) Int. Cl.
  *G01M 7/00*    (2006.01)
  *G01B 3/00*    (2006.01)
(52) U.S. Cl. ............................. 73/649; 73/664; 702/33
(58) Field of Classification Search ................. 73/649, 73/662, 663, 664, 665–672; 702/30, 33, 702/35, 56
See application file for complete search history.

(56) References Cited

U.S. PATENT DOCUMENTS

| 5,388,056 | A | 2/1995 | Horiuchi et al. | |
| 6,575,037 | B1* | 6/2003 | Momoi et al. ................. | 73/633 |
| 6,629,042 | B1* | 9/2003 | Yamagishi et al. ........... | 702/42 |
| 6,697,682 | B1* | 2/2004 | Dozono et al. ................ | 700/55 |
| 6,718,270 | B1* | 4/2004 | Horiuchi et al. .............. | 702/56 |
| 6,721,668 | B1* | 4/2004 | Momoi et al. ................. | 702/54 |
| 6,742,393 | B1* | 6/2004 | Ito .............................. | 73/662 |
| 6,752,019 | B1 | 6/2004 | Horiuchi et al. | |
| 6,763,311 | B1* | 7/2004 | Inoue et al. .................. | 702/56 |
| 6,779,404 | B1* | 8/2004 | Brincker et al. .............. | 73/659 |

FOREIGN PATENT DOCUMENTS

| JP | 5-332876 A | 12/1993 |
| JP | 2002-214068 A | 7/2002 |

OTHER PUBLICATIONS

Koichi Takanasi et al., "Analysis of Nonlinear Response of Structure to Earthquake by Computer-Testing Machine Online System", vol. 288, Feb. 1980, pp. 115-123.
Masayoshi Nakashima et al., "Integration Method Capable of Controlling Experimental Error Growth in Substructure Pseudo Dynamic Test", vol. 454, Dec. 1993, pp. 61-70.

* cited by examiner

*Primary Examiner*—Hezron Williams
*Assistant Examiner*—Jacques Saint-Surin
(74) *Attorney, Agent, or Firm*—Crowell & Moring LLP

(57) ABSTRACT

A vibration test system for structures comprises a vibration exciter that vibrates a real model portion, a load meter that measures a load, and a computer that receives a numerical model representing a numerical model portion. The computer includes a block that calculates a displacement, which is made in a predetermined time after completion of measurement, according to a load value and an external force value. A signal production block produces a command signal using as a target value the displacement calculated by the displacement calculation block. A step control block controls the displacement calculation block and signal production block so that they will act cyclically. The displacement calculation block uses an $\alpha OS$ method to time integrate a solution of a vibrational equation.

11 Claims, 5 Drawing Sheets

VIBRATION TEST SYSTEM AND METHOD FOR STRUCTURES

CLAIM OF PRIORITY

The present application claims priority from Japanese Application JP2004-010047 filed on Jan. 19, 2004, the contents of which are hereby incorporated by reference into this application.

BACKGROUND OF THE INVENTION

The present invention relates to a vibration test system for structures and a vibration test method implemented therein. In particular, the present invention is concerned with a vibration test system and method for structures that perform in combination a vibration test on part of a structure and numerical analysis of a vibrational response.

A vibration test in which a vibration test on part of a structure and numerical analysis of a vibrational response are performed in combination is called a "actuator-computer online test." An example of an actuator-computer online test system is described in, for example, the report collection published from Architectural Institute of Japan (Vol. 288, 1980, pp. 115–124). As described in the literature, a central difference method that is one of explicit time integral approaches obviating the necessity of convergence is adopted as time integration required for numerical analysis of a vibrational response.

Moreover, in order to sophisticate the time integration required for numerical analysis of a vibrational response employed in an actuator-computer online test, a technology of adopting an αOS method that is one of mixed integral approaches of the explicit and implicit time integral approach is introduced in, for example, "Numerical Integration Method for Experimentation of Tentatively Moving a Substructure providing an Experimentation Error Control Effect" (report collection published from Architectural Institute of Japan, Vol. 454, pp. 61–71, 1993). The αOS method is a time integration method that is a mixture of an OS method which remains stable even when the calculation time interval is set to a large value, and an α method that is an implicit time integral approach for damping a high-order mode of vibration serving as a factor of an error. The αOS method is a time integration method suitable for the actuator-computer online test. According to the αOS method, a restoring force exerted by a structure to be assessed is divided into a linear component and a nonlinear component. The explicit time integral approach is applied to the nonlinear component of the restoring force exerted by the structure, and the implicit time integral approach is applied to the other component of the restoring force.

The central difference method is one of explicit time integral approaches for predicting a deformed state attained at a current time step from the deformed state observed at the previous time step. In the actuator-computer online test, a target displacement is obtained by calculating a vibrational response. An actuator is driven to cause the target displacement. When a reaction of a specimen is detected, the test proceeds to the next step. This procedure is repeated. The central difference method needs to determine a calculation time interval on the basis of the shortest natural period of a structure, of which reaction is to be calculated, because of restrictions imposed for stable condition.

Therefore, when a structure to be assessed is complex, it is necessary to not only increase the freedom in a vibrational equation but also reduce a calculation time interval along with a decrease in the natural period of the structure. This poses a problem in that a load on calculation increases. Moreover, when the calculation time interval is reduced, a change in a vibratory displacement caused by an actuator at a time step is diminished. This poses a problem in that precision in excited vibration deteriorates and an error in a high-order mode of vibration takes place.

Moreover, a method widely used for numerical analysis of a vibrational response is what is called an implicit time integral approach. According to the implicit time integral approach, a calculation time interval can be increased irrespective of the natural period of a structure to be assessed. However, the implicit time integral approach requires convergence of a deformed state attained at a current time step on the basis of a balance of forces at the current time step. When the structure to be assessed exhibits a nonlinear characteristic, the convergence becomes complex. Consequently, since an actuator must be driven according to the complex convergence process, the implicit time integral approach is unsuitable for the actuator-computer online test.

In order to improve the precision in the actuator-computer online test, there is a demand for a time integral approach capable of controlling an experimental error, which causes an error in a high-order mode of vibration, and of remaining stable despite a long interval between calculations.

In recent years, improvement in the aseismatic performance of an architectural structure or a plant structure or improvement in precision in assessing aseismatic strength has been demanded. Moreover, exploitation of an actuator-computer online test has been expected. The capability to assess more complex structures as well as the improvement in the precision in the assessment has been demanded. This causes a numerical model portion of a structure to become larger in size and more complex, and necessitates introduction of a nonlinear finite element method. Formulation based on an incremental equilibrium equation having as an unknown an incremental displacement between time steps has become the mainstream of time integration employed in numerical analysis of a vibrational response required by the nonlinear finite element method, because the formulation is superb in convergence.

In contrast, the αOS method adapted to an actuator-computer online test described in the aforesaid non-patent document "Numerical Integration Method for Experiment of Tentatively Moving a Substructure providing an Experimental Error Control Effect" is based on an equilibrium equation having as an unknown a displacement itself occurring at each time step. Therefore, the αOS method can handle only a linear model as a model representing a numerical model portion in practice.

BRIEF SUMMARY OF THE INVENTION

Accordingly, an object of the present invention is to highly precisely perform a vibration test, which is a mixture of a vibration test on part of a structure and numerical analysis of a vibrational response, though a numerical model portion of a structure is large in size and complex and exhibits a nonlinear characteristic.

In order to accomplish the above object, the present invention provides a vibration test system for structures comprising: a vibration exciting means for vibrating a real model portion that is a portion of a structure to be assessed; a load measuring means for measuring a load to be imposed on the real model portion by the vibration exciting means; and a computer that receives a numerical model representing a numerical model portion other than the real model portion, also receives a load value measured by the load measuring means; and produces and transmits a command signal, which is transferred to the vibration exciting means according to the received model and load value. The computer comprises: a command displacement calculating means for calculating a displacement of the real model portion in a predetermined time after completion of measurement by the load measuring means; a command signal producing means for producing the command signal, which is transmitted to the vibration exciting means, using as a target value the displacement calculated by the command displacement calculating means; and a step control means for controlling the vibration exciting means, the load measuring means, the command displacement calculating means, and the command signal producing means so that they will act cyclically. The command displacement calculating means uses the αOS method for time integration to solve a vibrational equation providing a displacement, and an equilibrium equation is solved based on an increment of the solution of the vibrational equation obtained at each time step from the solution thereof obtained at the previous time step.

The present invention provides a vibration testing method for structures wherein: a vibration exciting means vibrates a real model portion that is a portion of a structure to be assessed; a load measuring means measures a load to be imposed on the real model portion by the vibration exciting means; and a computer receives a numerical model representing a numerical model portion of the structure other than the real model portion, receives a load value measured by the load measuring means, and produces a command signal, which is transferred to the vibration exciting means, according to the received model and value. Herein, based on the load value measured by the load measuring means and a set external force value, a command displacement calculating means calculates a displacement of the real model portion in a predetermined time after completion of measurement by the load measuring means. A command signal producing means produces the command signal, which is transferred to the vibration exciting means, using as a target value the displacement calculated by the command displacement calculating means. A step control means controls the vibration exciting means, load measuring means, command displacement calculating means, and command signal producing means so that they will act cyclically. For calculation of the displacement of the real model portion, the command displacement calculating means uses the αOS method for time integration to solve a vibrational equation that provides a displacement. An equilibrium equation is solved based on an increment of the solution of the vibrational equation obtained at each time step from the solution thereof obtained at the previous time step.

DETAILED DESCRIPTION OF THE INVENTION

Figure 1:
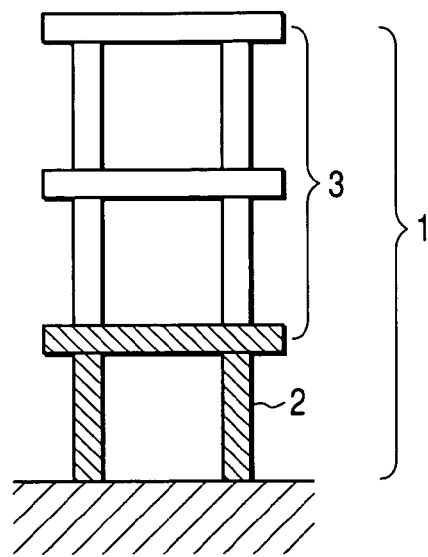
FIG. 1 illustratively shows a structure to be assessed that is employed in a comparative example and embodiments of the present invention.
Figure 2:
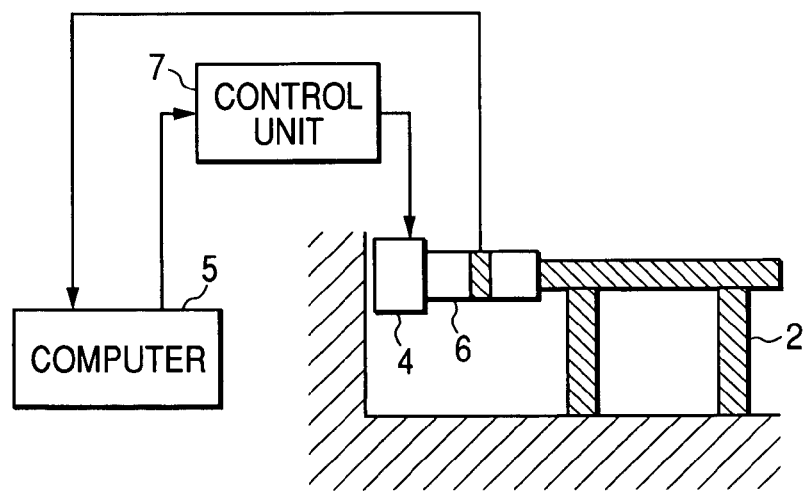
FIG. 2 is an explanatory diagram concerning a vibration test system and method for structures in accordance with the comparative example.
Figure 3:
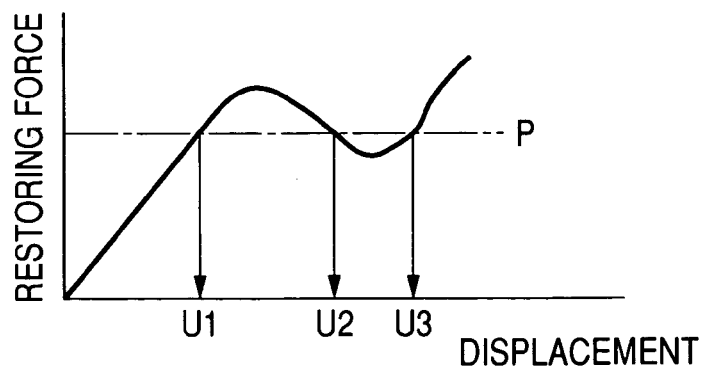
FIG. 3 is an explanatory diagram concerning relationship between a displacement and a load of the structure to be assessed.

Referring to the drawings, a comparative example and a plurality of embodiments of the present invention will be described below. The same reference numerals in the drawings will denote identical or equivalent components. FIG. 1 illustratively shows a structure to be assessed which is employed in the comparative example and the embodiments of the present invention. FIG. 2 is an explanatory diagram concerning a vibration test system and method for structures in accordance with the comparative example. FIG. 3 is an explanatory diagram concerning relationship between a displacement and a load of the structure to be assessed.

A structure 1 to be assessed, that is, an object whose vibrational response is assessed comprises, as shown in FIG. 1, a real model portion 2 that is an object of a vibration test, and a numerical model portion 3 to be modeled with numerical values. The numerical model portion 3 is a portion other than the real model portion 2. The real model portion 2 is, as shown in FIG. 2, vibrated by a vibration exciter 4. The vibration exciter 4 is provided with a load meter 6. The load meter 6 measures a reaction applied from the real model portion 2 to the vibration exciter 4. The load meter 6 serves as a load measuring means and may be incorporated in the vibration exciter 4. The measured reaction is transferred to a computer 5. Moreover, the numerical model portion 3 is modeled with numerical values and the resultant model is transferred to the computer 5. The computer 5 calculates a command signal, and the command signal is transferred to a control unit 7. The control unit 7 serves as a control means for controlling the vibration exciter 4. Based on the received command signal, the control unit 7 controls the vibration exciter 4. The control unit 7 may be incorporated in the computer 5.

The computer 5 repeatedly performs calculation of an external force vector representing an external force such as an earthquake, calculation of a vibrational response made to the external force vector by the numerical model in a certain time, and calculation of a command value, which is issued to the vibration exciter 4, based on the result of the calculation of a vibrational response. Consequently, a vibrational response made by the combination of the real model portion 2 and numerical model portion 3 is assessed by performing a vibration test on the real model portion 2 alone.

The calculation of a vibrational response performed by the computer 5 in the comparative example will be described below. The description will be made on the assumption that the structure 1 to be assessed which is shown in FIG. 2 is regarded as an object of experiment. A fundamental formula of a vibrational equation expressing a vibration made by the structure 1 to be assessed which includes the real model portion 2 is provided as a formula (1) below.

$$MA+CV+KX=P \tag{1}$$

where M denotes a mass coefficient, C denotes a damping coefficient, K denotes a stiffness coefficient, A denotes an acceleration, V denotes a velocity, X denotes a displacement, P denotes an external force, MA denotes an inertia, CV denotes a damping force, and KX denotes a restoring force.

A method of numerical calculation expressed as the formula (1) includes various numerical algorithms. For example, a central difference method is often employed in a conventional actuator-computer online test. The central difference method requires a calculation time interval, $\Delta t$, and the shortest natural period Tmin of a structure that is an object of calculation to meet the relationship of $\Delta t < Tmin/\pi$ for the purpose of ensuring stability. Therefore, when the natural period Tmin to be assessed is quite short, the calculation time interval, $\Delta t$, must be reduced. This poses a problem in that a load on calculation increases. Moreover, a minute vibratory displacement must be caused. This degrades precision in vibration and brings about a high-order mode of vibration.

In order to solve the above problems, adoption of an αOS method as a numerical integration method expressed as the formula (1) is conceivable. The αOS method is a combination of an OS method making it possible to increase a calculation time interval, and an α method making it possible to control occurrence of the high-order mode of vibration. The effects of the αOS method will be described below by presenting the effects of the OS method and a α method respectively. Furthermore, a fundamental formula required by the αOS method will be described below.

When the OS method is adapted to an actuator-computer online test, the calculation time interval can be increased irrespective of the shortest natural period of the structure 1 to be assessed. The reason why the calculation time interval can be increased will be described below. The OS method divides the nonlinear stiffness K of an entire object of assessment into a linear stiffness $K^0$ independent of a history and a nonlinear stiffness $K^1$ dependent on the history. An implicit time integral approach that is unconditionally stable, for example, the Newmark β method is applied to the linear stiffness term. An explicit integral approach, for example, a predictor corrector method is applied to the nonlinear stiffness term. A formula (2) is the fundamental formula required by the OS method, applied at a temporal step n+1, and produced by rewriting the formula (2). Assume that X, V, and A denote a displacement, a velocity, and an acceleration respectively required by the implicit time integral approach, and that X* denotes a displacement required by the explicit time integral approach.

$$MA_{n+1} + CV_{n+1} + K^0 X_{n+1} + K^1 X^*_{n+1} = P_{n+1} \quad (2)$$

where $MA_{n+1}$ denotes an inertia, $CV_{n+1}$ denotes a damping force, $K^0 X_{n+1}$ denotes a linear restoring force, $K^1 X^*_{n+1}$ denotes a nonlinear restoring force, $K^0$ denotes a coefficient of linear stiffness, $K^1$ denotes a coefficient of nonlinear stiffness, $P_{n+1}$ denotes an external force at a temporal step n+1, $A_{n+1}$ denotes an acceleration observed at the temporal step n+1 and required by the implicit time integral approach, $V_{n+1}$ denotes a velocity observed at the temporal step n+1 and required by the implicit time integral approach, $X_{n+1}$ denotes a displacement observed at the temporal step n+1 and required by the implicit time integral approach, and $X^*_{n+1}$ denotes a displacement observed at the temporal step n+1 and required by the explicit time integral approach.

According to the OS method, the displacement X* required by the explicit time integral approach is inferred according to any method but not obtained through convergence. For example, when the predictor corrector method is adopted, the displacement X* at the temporal step n+1 is explicitly expressed as a formula (3) below using a displacement $X_n$, a velocity $V_n$, and an acceleration $A_n$ observed as a temporal step n and required by the implicit time integral approach. Incidentally, γ and β denotes auxiliary parameters, and $\Delta t$ denotes a calculation time interval.

$$X^*_{n+1} = X_n + \Delta t V_n + \frac{\Delta t^2}{2}(1-2\beta)A_n \quad (3)$$

The displacement $X_{n+1}$ and velocity $V_{n+1}$ required by the implicit time integral approach and observed at the temporal step n+1 are expressed as formulae (4) and (5) according to the Newmark β method.

$$X_{n+1} = X^*_{n+1} + \Delta t^2 \beta A_{n+1} = X_n + \Delta t V_n + \Delta t^2/2(1-2\beta)A_n + \Delta t^2 \beta A_{n+1} \quad (4)$$

$$V_{n+1} = V_n + \Delta t(1-\gamma)A_n + \Delta t \gamma A_{n+1} \quad (5)$$

Stability is determined based on a regression function expressed by a formula (6) that is obtained by assigning the formulae (3), (4), and (5) to the formula (2) on the assumption that the external force provided by the formula (2) is 0 and the object of assessment is regarded as a single-degree-of-freedom system.

$$X_{n+1} = A^* X_n \quad (6)$$

where A* denotes an amplification matrix.

Here, A* denotes what is called an amplification matrix. If the maximum absolute value of the eigenvalue λi of A* is equal to or smaller than 1, a numerical integration error is not amplified. Therefore, $X_{n+1}$ provided by the formula (6) is stable. As for the formula (2), if γ is equal to or larger than ½ and $\beta=(\gamma+½)^2/4$ is established, the solution of the formula (2) is unconditionally stable. For example, γ may be set to ½ and β may be set to ¼. According to the OS method, since a time integral is unconditionally stable, the interval $\Delta t$ can be freely set to any value.

Next, the reason why the a method that is an implicit time integral approach is adopted in order to damp a high-frequency component will be described below. The fundamental formula required by the α method is provided as a formula (7) produced by introducing an auxiliary parameter α to the formula (1) with respect to a temporal step n+1. For brevity's sake, the formula (7) is defined with the structure to be assessed regarded as a single-degree-of-freedom system, and the term of a damping coefficient is omitted.

$$MA_{n+1} + (1+\alpha)KX_{n+1} - \alpha KX_n = P_{n+1} \quad (7)$$

The Newmark β method is applied to the fundamental formula required by the α method, and the formulae (4) and (5) are assigned to the formula (7). Consequently, $X_{n+1}$ and $X_n$ are related to each other by the amplification matrix A* as they are expressed in the formula (6). Under the condition that the maximum absolute value of the eigenvalue λi of A* is equal to or smaller than 1, when $\gamma=½-\alpha$ and $\beta=(1-\alpha)^2/4$ are established, if α is equal to or larger than $-½$ and equal to or smaller than 0, the solution of the formula (7) is unconditionally stable. Moreover, the frequency characteristic of a numerical integration error is determined with the conjugate roots λ1 and λ2 of the amplification matrix A*. Assuming that a denotes a real part of the conjugate root λ1 or λ2 and bi denotes an imaginary part thereof, if $\lambda 1, 2 = a \pm ib$ is established, a damping ratio ξ* derived from the numerical integration error is provided as a formula (8) below. Incidentally, i denotes an imaginary unit.

$$\xi^* = -\frac{\ln(a^2+b^2)}{2\bar{\Omega}}, \bar{\Omega} = \arctan(b/a) \quad (8)$$

where $\xi^*$ denotes a damping ratio derived from a numerical integration error.

When the formula (8) is solved under the conditions of $\gamma=\frac{1}{2}-\alpha$ and $\beta=(1-\alpha)^2/4$, the formula (8) is rewritten into a formula (9) below. The smaller the natural frequency $(K/M)^{1/2}$ of a single-degree-of-freedom system is, the smaller the damping ratio $\xi^*$ is. The larger the natural frequency $(K/M)^{1/2}$ is, the larger the damping ratio $\xi^*$ is.

$$\xi^* = -\frac{\alpha(1+\alpha^2+2\alpha)}{8}\left(\sqrt{\frac{K}{M}}\right)^3 + O(\Omega^5) \quad (9)$$

Namely, a high-frequency component is damped but a low-frequency component is not deformed. As mentioned above, the higher-frequency component can be damped owing the a method that is an implicit time integral approach.

The ΔOS method employed as a time integration method in an actuator-computer online test performed by a variant of the present invention is a combination of the OS method and the a method. The fundamental formula produced with respect to a step n+1 is given as formula (10) below. Incidentally, X denotes a displacement required by the implicit time integral approach and X* denotes a displacement required by the explicit time integral approach. Hereinafter, the displacement required by the explicit time integral approach shall be referred to as a predictor displacement. The relationships expressed by the formulae (3) to (5) are applied to the fundamental formula (10), and time integration is performed.

$$MA_{n+1} + (1+\alpha)CV_{n+1} - \alpha CV_n + (1+\alpha)(K^0 X_{n+1} + K^1 X^*_{n+1}) - \alpha(K^0 X_n + K^1 X^*_n) = (1+\alpha)P_{n+1} - \alpha P_n \quad (10)$$

The left side of the formula (10) provides the sum of an inertia, a damping force weighted with α, and a restoring force weighted with α, while the right side thereof provides an external force weighted with α. Moreover, the restoring force is the sum of a restoring force proportional to a linear stiffness and a restoring force proportional to a nonlinear stiffness. However, in the present variant, the formula (10) expresses equilibrium attained at a current step. In an actuator-computer online test, the formula (10) is suitable to a case where only the real model portion 2 of the object of the test has the nonlinear stiffness and the remaining numerical model portion 3 has the linear stiffness. The formula (10) is unsuitable for a case where the numerical model portion 3 also exhibits the nonlinear stiffness. The reason will be described below.

Assuming that the fundamental formula of the formula (10) is adapted to an actuator-computer online test, each matrix is divided into a domain relevant to the specimen portion (real model portion 2) and a domain relevant to the other portion (numerical model portion 3). Furthermore, a formula (11) expresses the nonlinear stiffness of the real model portion 2 alone. For brevity's sake, a term expressing a damping force C is omitted. Subscripts t and m signify the relationships to the real model portion 2 and the numerical model portion 3 respectively.

$$\begin{bmatrix} M_{mm} & M_{mt} \\ M_{tm} & M_{tt} \end{bmatrix}\begin{bmatrix} A_{m,n+1} \\ A_{t,n+1} \end{bmatrix} + \quad (11)$$
$$(1+\alpha)\left(\begin{pmatrix} K_{mm} & K_{mt} \\ K_{tm} & K^0_{tt} \end{pmatrix}\begin{bmatrix} X_{m,n+1} \\ X_{t,n+1} \end{bmatrix} + \begin{pmatrix} 0 & 0 \\ 0 & K^1_{tt} \end{pmatrix}\begin{bmatrix} 0 \\ X^8_{t,n+1} \end{bmatrix}\right) - = (1+\alpha)P_{n+1} - \alpha P_n$$
$$\alpha\left(\begin{pmatrix} K_{mm} & K_{mt} \\ K_{tm} & K^0_{tt} \end{pmatrix}\begin{bmatrix} X_{m,n} \\ X_{t,n} \end{bmatrix} + \begin{pmatrix} 0 & 0 \\ 0 & K^1_{tt} \end{pmatrix}\begin{bmatrix} 0 \\ X^*_{t,n} \end{bmatrix}\right)$$

where $$\begin{bmatrix} M_{mm} & M_{mt} \\ M_{tm} & M_{tt} \end{bmatrix}$$

denotes a mass matrix, $$\begin{pmatrix} K_{mm} & K_{mt} \\ K_{tm} & K^0_{tt} \end{pmatrix}$$

denotes a matrix obtained by removing an element, which represents the nonlinear stiffness of a specimen portion, from a stiffness matrix representing an entire vibrating system, $$\begin{pmatrix} 0 & 0 \\ 0 & K^1_{tt} \end{pmatrix}$$

denotes a matrix containing an element that represents the nonlinear stiffness of the specimen portion, $P_{n+1}$ denotes an external force vector observed at a step n+1, $$\begin{bmatrix} A_{m,n+1} \\ A_{t,n+1} \end{bmatrix}$$

denotes an acceleration observed at the step n+1 and required by the implicit time integral approach, $$\begin{bmatrix} X_{m,n+1} \\ X_{t,n+1} \end{bmatrix}$$

denotes a displacement observed at the step n+1 and required by the implicit time integral approach, and $$\begin{bmatrix} 0 \\ X^*_{t,n+1} \end{bmatrix}$$

denotes a predictor displacement observed at the step n+1.

The matrix representing the nonlinear stiffness of the real model portion 2 and being included in the right side of the formula (11) is unknown and must be determined from the result of an experiment performed by loading the real model portion 2 on an experimenting machine. Assuming that a vector Ft,n+1 represents a reaction of the real model portion 2 made when the real model portion 2 is vibrated until it makes a displacement corresponding to the predictor displacement Xt,n+1*, the vector Ft,n+1 is, as expressed in a formula (12), obtained as a product of a matrix, of which elements represent the linear stiffness $K^0$ of the real model portion 2 and the nonlinear stiffness $K^1$ thereof, by the predictor displacement.

$$\begin{bmatrix} 0 \\ F_{t,n+1} \end{bmatrix} = \left( \begin{bmatrix} 0 & 0 \\ 0 & K^0_{tt} \end{bmatrix} + \begin{bmatrix} 0 & 0 \\ 0 & K^1_{tt} \end{bmatrix} \right) \begin{bmatrix} 0 \\ X^*_{t,n+1} \end{bmatrix} \quad (12)$$

where $$\begin{bmatrix} 0 \\ F_{t,n+1} \end{bmatrix}$$

denotes a vector representing a reaction of the specimen, and $$\begin{bmatrix} 0 & 0 \\ 0 & K^0_{tt} \end{bmatrix} + \begin{bmatrix} 0 & 0 \\ 0 & K^1_{tt} \end{bmatrix}$$

denotes a matrix whose elements represent the nonlinear stiffness $K^0$ of the specimen portion and the nonlinear stiffness $K^1$ thereof.

A vibrational equation required by the αOS method is provided as a formula (13), which has as an unknown a displacement observed at a temporal step n+1 and required by the implicit time integral approach, using the formulae (11) and (12).

$$\left( \frac{1}{\beta \Delta t^2} \begin{bmatrix} M_{mm} & M_{mt} \\ M_{tm} & M_{tt} \end{bmatrix} + (1+\alpha) \begin{pmatrix} K_{mm} & K_{mt} \\ K_{tm} & K^0_{tt} \end{pmatrix} \right) \begin{bmatrix} X_{m,n+1} \\ X_{t,n+1} \end{bmatrix} = \quad (13)$$

$$-(1+\alpha) \left( \begin{bmatrix} 0 \\ F_{t,n+1} \end{bmatrix} - \begin{pmatrix} 0 & 0 \\ 0 & K^0_{tt} \end{pmatrix} \begin{bmatrix} 0 \\ X^*_{t,n+1} \end{bmatrix} \right) + (1+\alpha)P_{n+1} -$$

$$\alpha P_n + \alpha \left( \begin{pmatrix} K_{mm} & K_{mt} \\ K_{tm} & K^0_{tt} \end{pmatrix} \begin{bmatrix} X_{m,n} \\ X_{t,n} \end{bmatrix} + \begin{bmatrix} 0 \\ F_{t,n} \end{bmatrix} - \right.$$

$$\left. \begin{pmatrix} 0 & 0 \\ 0 & K^1_{tt} \end{pmatrix} \begin{bmatrix} 0 \\ X^*_{t,n+1} \end{bmatrix} \right) + \frac{1}{\beta \Delta t^2} \begin{bmatrix} M_{mm} & M_{mt} \\ M_{tm} & M_{tt} \end{bmatrix} \left( \begin{bmatrix} X_{m,n} \\ X_{t,n} \end{bmatrix} + \right.$$

$$\left. \Delta t \begin{bmatrix} V_{m,n} \\ V_{t,n} \end{bmatrix} + \frac{\Delta t^2}{2}(1-2\beta) \begin{bmatrix} A_{m,n} \\ A_{t,n} \end{bmatrix} \right)$$

where $$\left( \frac{1}{\beta \Delta t^2} \begin{bmatrix} M_{mm} & M_{mt} \\ M_{tm} & M_{tt} \end{bmatrix} + (1+\alpha) \begin{pmatrix} K_{mm} & K_{mt} \\ K_{tm} & K^0_{tt} \end{pmatrix} \right)$$

denotes a coefficient matrix, $$\begin{bmatrix} X_{m,n+1} \\ X_{t,n+1} \end{bmatrix}$$

denotes an unknown displacement, and $$-(1+\alpha) \left( \begin{bmatrix} 0 \\ F_{t,n+1} \end{bmatrix} - \begin{pmatrix} 0 & 0 \\ 0 & K^0_{tt} \end{pmatrix} \begin{bmatrix} 0 \\ X^*_{t,n+1} \end{bmatrix} \right) + (1+\alpha)P_{n+1} - \alpha P_n +$$

$$\alpha \left( \begin{pmatrix} K_{mm} & K_{mt} \\ K_{tm} & K^0_{tt} \end{pmatrix} \begin{bmatrix} X_{m,n} \\ X_{t,n} \end{bmatrix} + \begin{bmatrix} 0 \\ F_{t,n} \end{bmatrix} - \begin{pmatrix} 0 & 0 \\ 0 & K^1_{tt} \end{pmatrix} \begin{bmatrix} 0 \\ X^*_{t,n} \end{bmatrix} \right) +$$

$$\frac{1}{\beta \Delta t^2} \begin{bmatrix} M_{mm} & M_{mt} \\ M_{tm} & M_{tt} \end{bmatrix} \left( \begin{bmatrix} X_{m,n} \\ X_{t,n} \end{bmatrix} + \Delta t \begin{bmatrix} V_{m,n} \\ V_{t,n} \end{bmatrix} + \frac{\Delta t^2}{2}(1-2\beta) \begin{bmatrix} A_{m,n} \\ A_{t,n} \end{bmatrix} \right)$$

denotes a known load.

If the coefficient matrix in the left side of the formula (13) is fixed, that is, if the coefficients of stiffness $K_{mm}$, $K_{mt}$, and $K_{tm}$ indicating the stiffness of the numerical model portion are fixed, the unknown displacement that is the unknown of the formula (13) can be calculated readily. However, when the coefficients of stiffness indicating the stiffness of the numerical model portion depend on the unknown displacement, that is, when the coefficient matrix in the left side of the formula (13) represents a nonlinear characteristic, an iterative operation must be performed according to a procedure described below.

(1) An unknown displacement is assumed.

(2) Coefficients of stiffness are predicted relative to the assumed unknown displacement.

(3) The coefficient matrix is calculated according to the formula (3).

(4) An inverse matrix of the coefficient matrix is produced.

(5) The right side of the formula (3) is multiplied by the inverse matrix in order to calculate a displacement.

(6) The above steps are repeated until the displacement and the assumed unknown displacement approach each other as closely as possible.

When the unknown displacement is obtained according to the present variant, if the displacement and a load have a relationship graphically shown in FIG. 3, a plurality of displacements U1, U2, and U3 may be calculated relative to a load P but a unique displacement may not be obtained. The present variant is therefore unsuitable for a case where the coefficient matrix included in the formula (13) represents a nonlinear characteristic, that is, the numerical model portion 3 has elements that exhibit the nonlinear characteristic.

Figure 4:
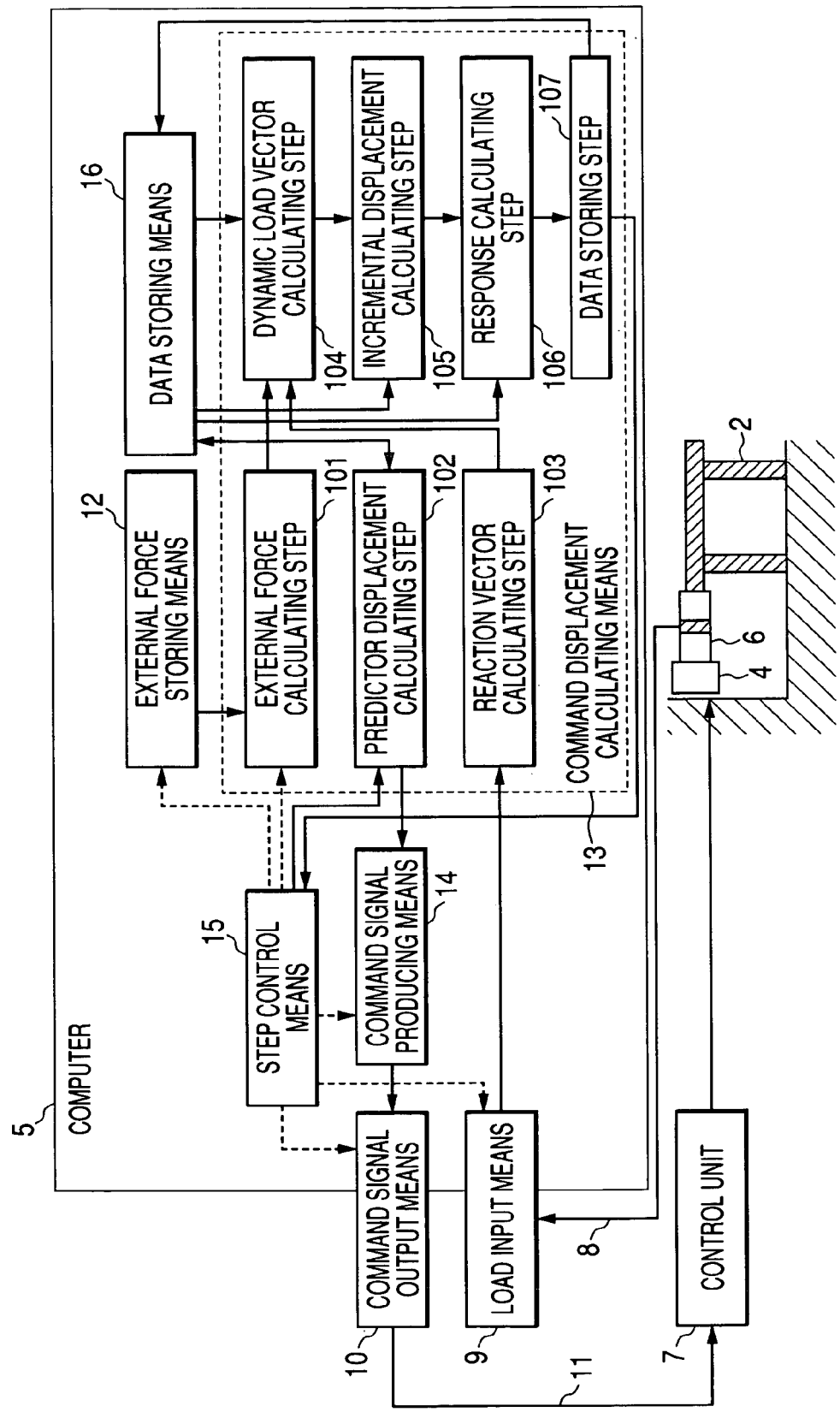
FIG. 4 to FIG. 6 are explanatory diagrams concerning vibration test systems and methods in accordance with various embodiments of the present invention.

Next, a vibration test system and method for structures in accordance with the first embodiment of the present invention will be described with reference to FIG. 1, FIG. 3, and FIG. 4. FIG. 4 is an explanatory diagram concerning the vibration test system and method for structures in accordance with the first embodiment of the present invention.

The first embodiment provides a vibration test system and method for structures for performing in combination a vibration test on part of a structure and numerical analysis of a vibrational response. Herein, the vibration test system and method for structures include a vibrational response analyzing means that can be used in practice when an actuator-computer online test is performed on a structure whose portion other than a real model portion also has elements that exhibit a nonlinear characteristic. The present embodiment is preferred in a case where a structure to be assessed is large in size and has a complex shape.

For numerical analysis of a nonlinear structure to which the present invention is adapted, a nonlinear finite element method is adopted. An iterative calculation algorithm is based on an incremental equilibrium equation that has an incremental displacement as an unknown, for example, the Newton Raphson method. When a configuration rule that determines the relationship between a stress and a strain depends on a path, the equilibrium equation must be incremental. Moreover, load control to be extended to calculate a small incremental displacement caused by a small incremental load is used differently from displacement control to be extended to calculate a small increment in a load causing a small incremental displacement, whereby a complex relationship between a load and a displacement like the one graphically shown in FIG. 3 can be followed.

If the numerical model portion 3 has a nonlinear element, introduction of a nonlinear finite element method to solution of an equation providing a displacement made by the numerical model portion 3 during an actuator-computer online test would prove effective. However, formulation making it possible to directly employ the combination of a nonlinear finite element method and a time integration method in the actuator-computer online test has not been achieved to date. In the present embodiment, formulation is achieved in order to combine an αOS method, which is a time integration method suitable for the actuator-computer online test, and the nonlinear finite element method. The formulation will be described below.

A fundamental formula having an increment as an unknown and being required by the αOS method is provided as a formula (14) below. The formula (14) has the unknown of the formula (10) expressed as an increment like Xn+1=Xn+ΔXn, and has relational expressions (15) and (16) assigned to the formula (10). A predictor can be calculated from the formula (3). Since the formula (14) is incremental, a convergent iterative method that is superior in convergence, for example, the Newton Raphson method can be adopted in order to follow a complex path.

$$K_{n+1}^{*} * \Delta X_n = F_{n+1}^{*} \text{ where} \quad (14)$$

$$K_{n+1}^{*} = \left(\frac{1}{\beta \Delta t^2}\begin{bmatrix} M_{mm} & M_{mt} \\ M_{tm} & M_{tt} \end{bmatrix} + (1+\alpha)\frac{\gamma}{\beta \Delta t}\begin{bmatrix} C_{mm} & C_{mt} \\ C_{tm} & C_{tt} \end{bmatrix} + (1+\alpha)\begin{bmatrix} K_{mm} & K_{tm} \\ K_{tm} & K_{tt}^{0} \end{bmatrix}\right)$$

denotes a coefficient matrix, $$\Delta \begin{bmatrix} X_{m,n} \\ X_{t,n} \end{bmatrix}$$

denotes an unknown incremental displacement, and $$F_{n+1}^{*} = \left((1+\alpha)\begin{bmatrix} P_{m,n+1} \\ P_{t,n+1} \end{bmatrix} - \alpha \begin{bmatrix} P_{m,n} \\ P_{t,n} \end{bmatrix}\right) -$$
$$\left(\begin{bmatrix} M_{mm} & M_{mt} \\ M_{tm} & M_{tt} \end{bmatrix}\begin{bmatrix} A_{m,n} \\ A_{t,n} \end{bmatrix} + \begin{bmatrix} C_{mm} & C_{mt} \\ C_{tm} & C_{tt} \end{bmatrix}\begin{bmatrix} V_{m,n} \\ V_{t,n} \end{bmatrix} + \begin{bmatrix} K_{mm} & K_{mt} \\ K_{tm} & K_{tt}^{0} \end{bmatrix}\begin{bmatrix} X_{m,n} \\ X_{t,n} \end{bmatrix}\right) - (1+\alpha)\left(\begin{bmatrix} 0 \\ F_{t,n+1} \end{bmatrix}\right) -$$
$$\begin{bmatrix} 0 & 0 \\ 0 & K_{tt}^{1} \end{bmatrix}\begin{bmatrix} 0 \\ X_{t,n+1}^{*} \end{bmatrix} - \alpha\left(\begin{bmatrix} 0 \\ F_{t,n} \end{bmatrix} - \begin{bmatrix} 0 & 0 \\ 0 & K_{tt}^{1} \end{bmatrix}\begin{bmatrix} 0 \\ X_{t,n}^{*} \end{bmatrix}\right) +$$
$$\begin{bmatrix} M_{mm} & M_{mt} \\ M_{tm} & M_{tt} \end{bmatrix}\left(\frac{1}{\beta \Delta t}V_n + \frac{1}{2\beta}A_n\right) -$$
$$(1+\alpha)\begin{bmatrix} C_{mm} & C_{mt} \\ C_{tm} & C_{tt} \end{bmatrix}\left(\Delta t\left(1 - \frac{\gamma}{2\beta}\right)A_n - \frac{\gamma}{\beta}V_n\right)$$

denotes a dynamic load vector.

$$\Delta A_n = \frac{1}{\beta \Delta t^2}\Delta X_n - \frac{1}{\beta \Delta t}V_n - \frac{1}{2\beta}A_n \quad (15)$$

$$\Delta V_n = \Delta t\left(1 - \frac{\gamma}{2\beta}\right)A_n + \frac{\gamma}{\beta \Delta t}\Delta X_n - \frac{\gamma}{\beta}V_n \quad (16)$$

A structure 1 to be assessed, that is, an object whose vibrational response is assessed which is employed in the present embodiment is identical to the one shown in FIG. 1 and described in relation to the comparative example. The structure 1 to be assessed comprises a real model portion 2 (specimen portion) that is an object of a vibration test, and a numerical model portion 3 (portion other than the real model portion) that is a portion to be modeled with numerical values.

The real model portion 2 is, as shown in FIG. 4, vibrated by a vibration exciter 4. The vibration exciter 4 includes a load meter 6 serving as a load measuring means. The load meter 6 measures a reaction applied from the real model 2 to the vibration exciter 4. The measured reaction is transferred to a computer 5. Moreover, the numerical model portion 3 is modeled with numerical values, and the model is transferred to the computer 5. The computer 5 calculates a command signal, and the command signal is transferred to a control unit 7. The control unit 7 serves as a control means for controlling the vibration exciter 4, and controls the vibration exciter 4 according to the received command signal.

The computer 5 includes an external force storing means 12 and an external force input means (not shown). A value of an external force applied to the object 1 whose vibrational response is assessed, such as, a seismic force is preserved in the computer, and can be transferred to the computer. The computer 5 must include either of the external force storing means 12 and external force input means.

The computer 5 includes a command displacement calculating means 13 that calculates a displacement, which occurs at a boundary point between the real model portion and numerical model portion in a predetermined time after completion of measurement by the load measuring means, according to a load value measured by the load measuring means and an external force value. The command displacement calculating means 13 uses the load value measured by the load measuring means 6 and the external force value preserved in the external force storing means 12 or transferred from the external force input means to calculate a displacement occurring at the boundary point on the boundary between the real model portion and numerical model portion in the predetermined time after the completion of load measurement. The calculated displacement is regarded as a command displacement.

The computer 5 includes a command signal producing means 14 that produces a control signal, which is transmitted to the vibration exciter 4, using as a target value the displacement at the boundary point calculated by the command displacement calculating means 13. The command signal producing means 14 produces a command signal, which is transmitted to the vibration exciter 4, according to the command displacement calculated by the command displacement calculating means 13, and transmits a command signal via a command signal output means 10. The command signal is transferred to the control unit 7, which controls the vibration exciter 4, over a command signal conveying means 11. The control unit 7 controls the vibration exciter 4 according to the command signal.

The computer 5 includes a step control means 15. The step control means 15 manages reception of an external force value, calculation of a command displacement based on which a command signal to be transmitted to the vibration exciter is produced, production of a command signal to be transmitted to the vibration exciter, transmission of the command signal to the vibration exciter, and reception of a measured load value. These actions are repeatedly performed until the number of time steps reaches a predefined number of time steps.

Incidentally, the load value or command signal to be transmitted to the vibration exciter is conveyed in the form of, for example, a voltage signal. At this time, a measured load conveying means 8 and a vibration exciter command signal conveying means 11 are realized with cables. A load input means 9 is realized with an A/D converter, and a command signal output means 10 is realized with a D/A converter. The signals may be provided in any other form. According to the form of the signals, the conveying means and input/output means become different.

The command displacement calculating means 13 calculates a signal according to a procedure described below and shown in FIG. 4. However, parameters required for the calculations described below, such as, a coefficient α, a calculation time interval Δt, a stiffness $K_{tt}^0$ exhibited by a linear element of the real model portion 2, and a numerical model representing the numerical model portion 3 are entered in advance using a data input means (not shown) included in the computer 5, and preserved in the data storing means 16 so that the parameters can be used during the procedure described below. Moreover, a displacement, a velocity, an acceleration, a predictor displacement, an external force, and a load required by an implicit time integral approach and measured at each time step are also preserved in the data storing means 16 so that they can be used during the procedure described below.

At an external force calculating step 101, an external force vector $P_{n+1}$ representing an external force observed at a step n+1 is calculated based on an external force such as a seismic force whose value is preserved in the external force storing means 12 or entered using the external force input means. The calculated external force vector $P_{n+1}$ is preserved in the data storing means 16. On the other hand, at a predictor displacement calculating step 103, a predictor displacement X*t,n+1 observed at the step n+1 is calculated according to the formula (3) on the basis of the values of the acceleration, velocity, and displacement that are observed at steps ending with a step n, required by the implicit time integral approach, and preserved in the data storing means 16. The calculated predictor displacement X*t,n+1 is preserved in the data storing means 16.

The predictor displacement X*t,n+1 calculated at the predictor displacement calculating step 102 is transferred to the command signal producing means 14. A command signal is then produced according to the command signal output means 10 and vibration exciter 4. The command signal produced by the signal producing means 14 is transmitted via the command signal output means 10, and transferred to the control unit 7, which controls the vibration exciter 4, over the command signal conveying means 11. The vibration exciter 4 is driven until a displacement corresponding to the predictor displacement X*t,n+1 is made. A measured load value measured by the load measuring means 6 is transferred to the computer 5 via the load input means 9 over the load conveying means 8.

At a reaction vector calculating step 103, a reaction vector Ft,n+1 representing a reaction of a specimen is calculated based on a load value transferred to the computer 5 via the load input means 9. The reaction vector Ft,n+1 is preserved in the data storing means 16. At a dynamic load vector calculating step 104, the reaction vector Ft,n+1 that represents a reaction of the specimen and is calculated at the reaction vector calculating step 103, the predictor displacement X*t,n+1 calculated at the predictor displacement calculating step 102, the external force vector Pn+1 calculated at the external force calculating step 101, and the values of the acceleration, velocity, displacement, predictor displacement, external force, and load that are required by the implicit time integral approach, observed at steps ending with an immediately preceding time step, and preserved in the data storing means are used to calculate a dynamic load vector F*n+1 according to the formula (14).

At an incremental displacement calculating step 105, an incremental displacement vector ΔXn required by the implicit time integral approach is assumed under certain conditions, and a dynamic stiffness matrix K*n+1 is produced based on the assumed vector. The dynamic stiffness matrix K*n+1 and the dynamic load vector F*n+1 calculated at the dynamic load vector calculating step 104 are used to calculate the vector ΔXn, which meets the formula (14), through iterative calculation or the like. At a response calculating step 106, the incremental displacement vector ΔXn required by the implicit time integral approach and calculated at the incremental displacement calculating step 105 and response values observed at time steps ending with the previous time step and preserved in the data storing means 16 are used to calculate an incremental velocity vector ΔVn and an incremental acceleration vector ΔAn that are required by the implicit time integral approach, and a response displacement vector Xn+1, a response velocity vector Vn+1, and a response acceleration vector An+1 that are required by the implicit time integral approach and observed at the current step n+1.

At a data storing step 107, the response values calculated at the response calculating step 106 are preserved in the data storing means 16. The step control means 15 increments the number of time steps, which start with time step 0, by one at every repetition of the steps starting with the external force calculating step 101 and ending with the data storing step 107. The steps are repeatedly executed until a pre-designated time step comes.

According to the present embodiment, even when a calculation time interval is increased, an actuator-computer online test can be achieved stably with an experimental error, which may bring about a high-order mode of vibration, suppressed. Furthermore, according to the present embodiment, an equilibrium equation having an incremental displacement as an unknown is used as a fundamental formula. Even when the numerical model portion other than the specimen portion exerts a nonlinear restoring force, a convergent iterative method permitting successful convergence can be adopted. Consequently, even when the numerical model portion is large in size and exhibits a nonlinear characteristic, an analytic load will not be increased and the inability to converge a value will not occur but an actuator-computer online test can be achieved highly precisely. The present invention adopts the Newmark β method as an implicit time integration method. Alternatively, any other implicit time integral approach may be adopted. Moreover, an unknown of an equation required by the implicit time integral approach is an incremental displacement. Alternatively, an incremental velocity or an incremental acceleration may be adopted as the unknown.

Figure 5:
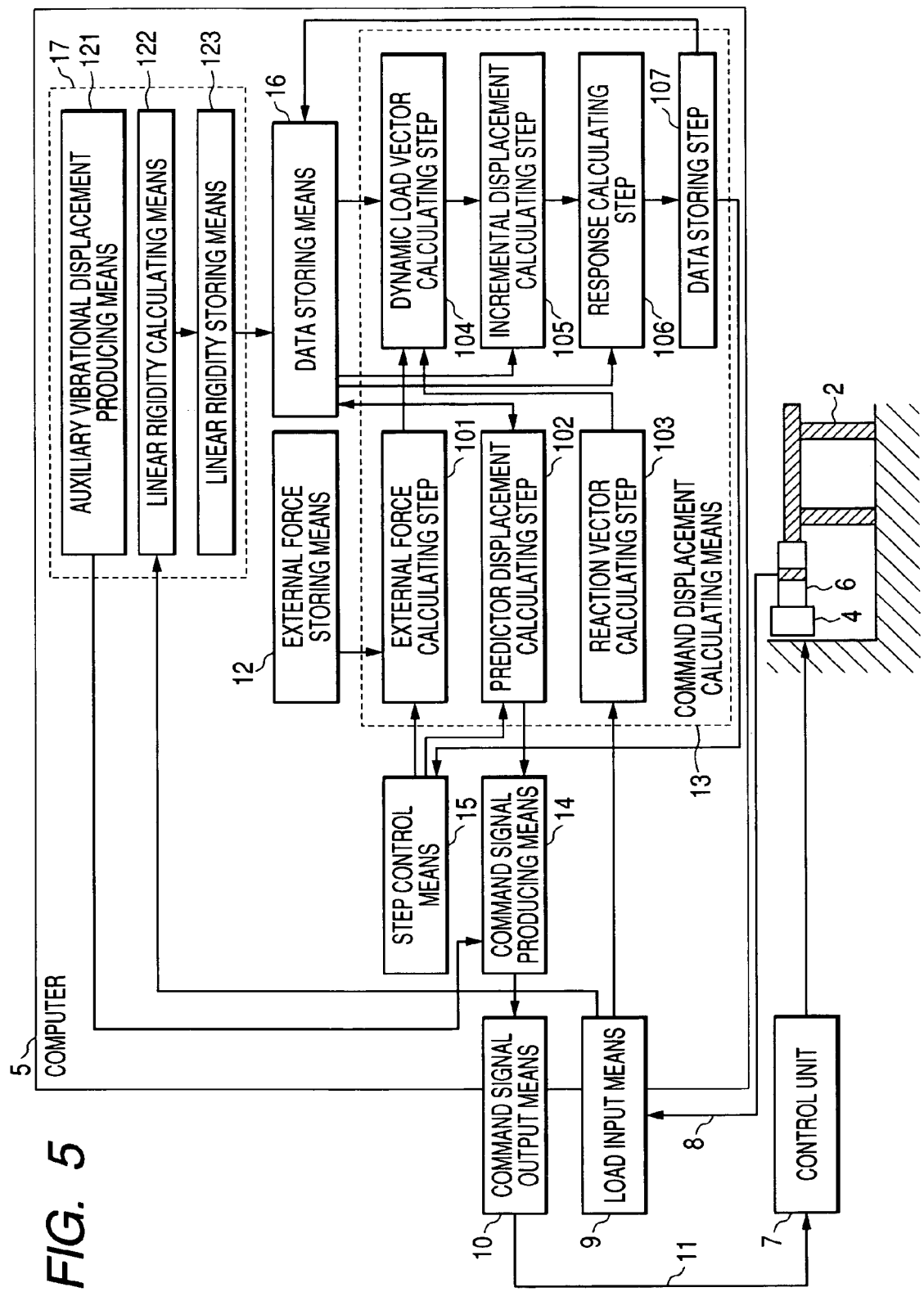

Next, the second embodiment of the present invention will be described with reference to FIG. 5. FIG. 5 is an explanatory diagram concerning a vibration test system and method for structures in accordance with the second embodiment of the present invention. The second embodiment is different from the first embodiment in a point described below. The second embodiment is fundamentally identical to the first embodiment in the other points.

According to the second embodiment, an experiment preparing means A17 for calculating a matrix $K_{tt}^0$ to be assigned to the formula (14) is added to the command displacement calculating means 13 included in the first embodiment. The experiment preparing means A17 comprises an auxiliary vibratory displacement producing means 121, a linear stiffness calculating means 122, and a linear stiffness storing means 123. The experiment preparing means A17 repeats a loop described below by the number of times equivalent to the number of degrees of freedom. Herein, when the degrees of freedom j shall range from a single degree of freedom to n degrees of freedom, the matrix $K_{tt}^0$ has n rows and n columns.

(1) The auxiliary vibratory displacement producing means 121 produces an auxiliary vibratory displacement vector representing a displacement Xp along the axes determined with the degrees of freedom j and representing a null displacement along the other axes.

(2) Based on the auxiliary vibratory displacement, the command signal producing means 14 produces a command signal.

(3) The command signal is transferred to the control unit 7, which controls the vibration exciter 4, via the command signal output means 10, whereby the vibration exciter 4 is driven.

(4) The load measuring means 6 measures a reaction of the real model portion 2.

(5) The value of the reaction of the real model portion 2 is transferred to the computer 5 via the load input means 9.

(6) The linear stiffness calculating means 122 uses the components Rkj (k ranges from 1 to n) of the reaction of the real model portion 2, which are represented by the elements of a K matrix, and the auxiliary vibratory displacement Xp to calculate linear stiffness $K_{tt}^0 kj=Rkj/Xp$ (where k ranges from 1 to n).

(7) The linear stiffness storing means 123 preserves the linear stiffness $K_{tt}^0 kj$ (where k ranges from 1 to n) in the data storing means 16. The linear stiffness are preserved in the data storing means 16 and used to calculate a displacement by the command displacement calculating means 13.

(8) The above steps (1) to (7) are repeated by the number of times corresponding to the number of degrees of freedom.

According to the second embodiment, the linear stiffness of the specimen portion can be precisely and readily assessed during an actuator-computer online test. This leads to improvement in testing efficiency and precision.

Figure 6:
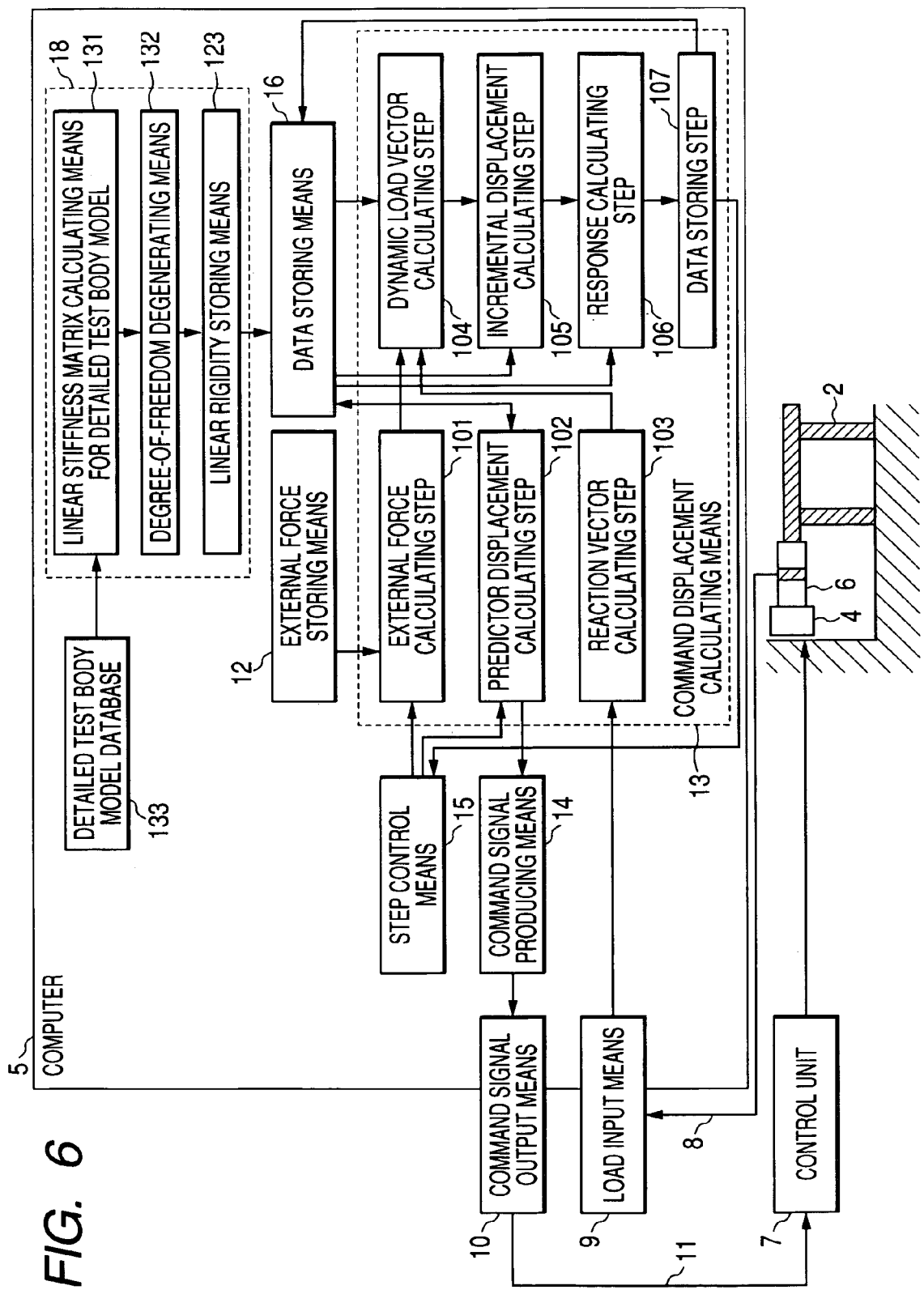
Figure 7:
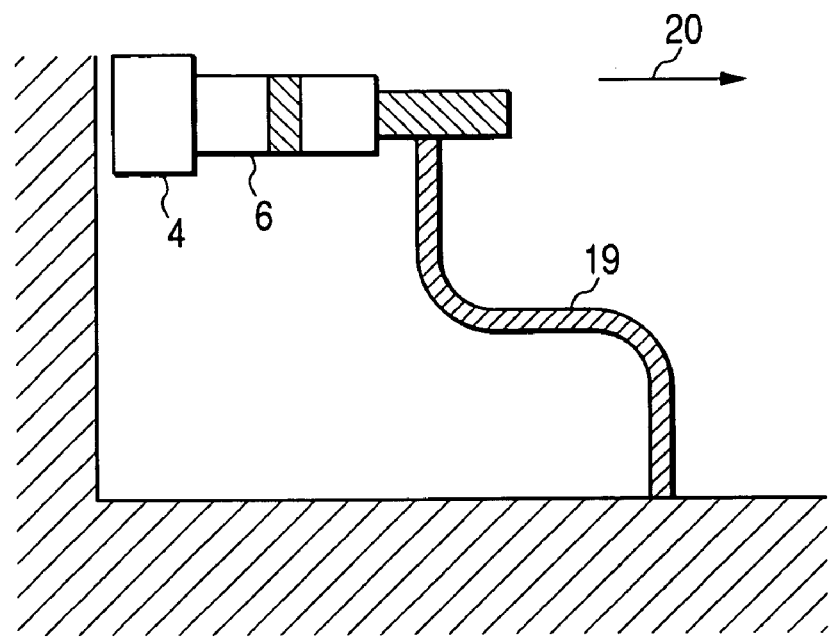
FIG. 7 to FIG. 8 are explanatory diagrams concerning a vibrating portion and a specimen included in the embodiment shown in FIG. 6.
Figure 8:
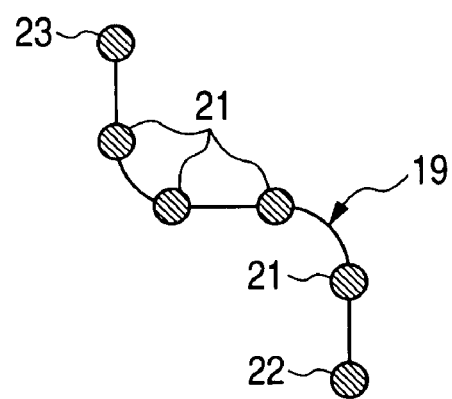

Next, the third embodiment of the present invention will be described with reference to FIG. 6 to FIG. 8. FIG. 6 is an explanatory diagram concerning a vibration test system and method for structures in accordance with the third embodiment of the present invention. FIG. 7 is an explanatory diagram showing an exciter assembly included in the third embodiment. FIG. 8 is an explanatory diagram showing divisions of a specimen employed in the third embodiment. The third embodiment is different from the first embodiment in a point described below, but fundamentally identical to the first embodiment in the other points.

According to the third embodiment, an experiment preparing means B18 for calculating a matrix $K_{tt}^0$ to be assigned to the formula (14) is added to the command displacement calculating means 13 included in the first embodiment. The experiment preparing means B18 comprises a linear stiffness matrix calculating means 131 for calculating a linear stiffness matrix representing a detailed model of a specimen, a degree-of-freedom degenerating means 132, and a linear stiffness storing means 123. Moreover, the third embodiment includes a database 133 in which a detailed model of a specimen is recorded. Hereinafter, a specimen portion 19 (see FIG. 7) shaped like a curved beam is taken for instance. The entire specimen portion 19 is regarded as a real model portion. Referring to FIG. 7, one vibration exciter 4 can vibrate the specimen portion in an X direction 20.

The linear stiffness matrix calculating means 131 for calculating a matrix that represents the linear stiffness of a detailed model of a specimen references the database 133, in which the detailed model of the specimen is recorded, so as to calculate a detailed linear stiffness matrix representing the specimen portion 19. In this case, the specimen portion 19 may be represented by a numerical model having an appropriate number of divisions according to a finite element method or the like, and a matrix whose elements represent the stiffness at points included in the respective divisions may be produced. Assuming that the number of points is n and the number of degrees of freedom at each point, that is, the number of axes along which the specimen can deform at each point is m, a linear stiffness matrix having n*m elements in rows and in columns and representing the detailed model of the specimen is produced. The specimen portion 19 shown in FIG. 7 is, as shown in FIG. 8, modeled with numerical values representing the elements of the beam according to the finite element method, and divided into n points 21. Thus, a numerical model of the specimen portion is produced. In this case, as mentioned above, the linear stiffness matrix having n*m elements in rows and in columns and representing the detailed model of the specimen is produced.

Next, the degree-of-freedom degenerating means 132 will be described. In an actuator-computer online test, one specimen portion 19 is represented with two points of a fixed point 22 and a vibrated point 23 and behaves as if it were formed with one element. If the number of degrees of freedom at each point, that is, the number of axes along which the specimen portion can be vibrated at each point is m', the specimen portion is treated as a virtual element having 2 m' degrees of freedom. In FIG. 7, since the specimen portion 19 can be vibrated one axis defining the X direction 20, the specimen portion must be treated as a two-degrees-of-freedom vibrating system in the actuator-computer online test. The degree-of-freedom degenerating means 132 uses the linear stiffness matrix, which represents the detailed model of the specimen, to calculate a degenerated linear stiffness matrix, which represents a vibrating system with the number of degrees of freedom required for the actuator-computer online test, by applying, for example, a Guyan degeneration method. The linear stiffness storing means 123 preserves the degenerated linear stiffness matrix, which is calculated by the degree-of-freedom degenerating means 132, so that the command displacement calculating means 13 can utilize the degenerated linear stiffness matrix. According to the third embodiment, the linear stiffness of the specimen portion 19 that is assessed in the actuator-computer online test adopting the αOS method can be calculated highly precisely and readily. Consequently, the efficiency and precision in the test can be improved.

Incidentally, in the foregoing embodiments, the number of real model portions 2 and the number of vibration exciter 4 are 1 s. Alternatively, one real model portion may be vibrated by a plurality of vibration exciters. Moreover, a plurality of real model portions 3 may be included. Moreover, a portion joined to a footing is regarded as a partial structure or an object of a vibration test. The present invention is not limited to the portion but may be applied to any portion of a structure. Moreover, one computer has been described to be used for calculations. As long as the foregoing actions can be realized, the actions may be assigned to a plurality of computers and the plurality of computers may transfer data to or from one another. Moreover, the computer is not limited to a type having one CPU but may be a parallel computer having a plurality of CPUs.

Furthermore, a data input/output device and a display device included in the computer incorporated in each of the aforesaid embodiments have not been described. Noted is that the computer includes an ordinary input/output device and an ordinary display device. Moreover, in the aforesaid embodiments, a vibrational response of a numerical model portion is calculated. The results of the calculation may be preserved in a storage device incorporated in or associated with the computer, and handled after completion of a test. Otherwise, the results of the calculation may be sequentially transmitted to equipment outside the computer during the test.

Moreover, the embodiments have been described to employ a uniaxial vibration exciter. In reality, a vibration exciting method should preferably be determined based on the freedom in determining the boundary value of a numerical model. For example, a six-axis vibration exciter may be adopted. Furthermore, the second and third embodiment may be combined. In this case, a vibration test system and method for structures having the advantages of both the second and third embodiment can be provided.

According to the constituent features of the present invention, there are provided a vibration test system and method for structures in which: when a vibration test includes a vibration test on part of a structure and numerical analysis of a vibrational response, even if a numerical model portion is large in size and has a complex nonlinear shape, the vibration test can be achieved highly precisely.

The preferred embodiments described herein are therefore illustrative and not restrictive. The scope of the invention being indicated by the appended claims and all variations which come within the meanings of the claims are intended to be embraced therein.

What is claimed is:

1. A vibration test system for structures comprising a vibration exciting means for vibrating a real model portion that is a portion of a structure to be assessed, a load measuring means for measuring a load that is imposed on the real model portion by the vibration exciting means, and a computer that receives a numerical model representing a numerical model portion that is a portion of the structure to be assessed other than the real model portion, receives a load value measured by the load measuring means, produces a command signal, which is transmitted to the vibration exciting means, according to the received model and value, wherein the computer comprises:

a command displacement calculating means for calculating a displacement, which is made by the real model portion in a predetermined time after completion of measurement by the load measuring means, according to the load value measured by the load measuring means and an external force value;

a command signal producing means for producing a command signal, which is transmitted to the vibration exciting means, using as a target value the displacement calculated by the command displacement calculating means; and a step control means for controlling the vibration exciting means, the load measuring means, the command displacement calculating means, and the command signal producing means so that they will act cyclically, wherein:

the command displacement calculating means uses an αOS method to time integration to solve a vibrational equation that provides a displacement; and the command displacement calculating means solves an equilibrium equation on the basis of an increment of the solution of the vibrational equation obtained at each time step from the solution thereof obtained at the previous time step.

2. The vibration test system for structures according to claim 1, wherein:

the command displacement calculating means calculates a displacement, which occurs at a boundary point between the real model portion and the numerical model portion in a predetermined time after completion of measurement by the load measuring means, according to the load value measured by the load measuring means and the external force value;

the command displacement calculating means solves an equilibrium equation on the basis of an increment of the solution of the vibrational equation obtained at each time step from the solution thereof obtained at the previous time step; and the command signal producing means produces a command signal, which is transmitted to the vibration exciting means, using as a target value the displacement at the boundary point calculated by the command displacement calculating means.

3. The vibration test system for structures according to claim 1, wherein:

the computer further comprises a load input means for transferring the load value measured by the load measuring means to the command displacement calculating means, and a command signal output means for transmitting the command signal produced by the command signal producing means to the vibration exciting means; and the step control means controls the load input means and the command signal output means so that they will act synchronously with the cycle of the actions performed by the vibration exciting means, load measuring means, command displacement calculating means, and the command signal producing means.

4. The vibration test system for structures according to claim 1, wherein the computer further comprises a data storing means for preserving a value of a coefficient α, a calculation time intervals, a stiffness of an element of the real model portion exhibiting a linear characteristic, and a numerical model that represents the numerical model portion, so that the command displacement calculating means can use them to calculate a displacement.

5. The vibration test system for structures according to claim 4, wherein the data storing means preserves a displacement, a velocity, an acceleration, a predictor displacement, an external force, and a load, which are required by an implicit time integral approach and obtained at each time step at which the command displacement calculating means calculates a displacement, so that the command displacement calculating means can use them to calculate a displacement.

6. The vibration test system for structures according to claim 1, wherein the command displacement calculating means uses the following formulae (14) and (3) and their definitions to calculate a displacement:

$$K_{n+1}^* \ast \Delta X_n = F_{n+1}^* \text{ where} \tag{14}$$

$$K_{n+1}^* = \left(\frac{1}{\beta \Delta t^2}\begin{bmatrix} M_{mm} & M_{mt} \\ M_{tm} & M_{tt} \end{bmatrix} + (1+\alpha)\frac{\gamma}{\beta \Delta t}\begin{bmatrix} C_{mm} & C_{mt} \\ C_{tm} & C_{tt} \end{bmatrix} + (1+\alpha)\begin{bmatrix} K_{mm} & K_{tm} \\ K_{tm} & K_{tt}^0 \end{bmatrix}\right)$$

denotes a coefficient matrix, $$\Delta \begin{bmatrix} X_{m,n} \\ X_{t,n} \end{bmatrix}$$

denotes an unknown incremental displacement, and $$F_{n+1}^* = \left((1+\alpha)\begin{bmatrix} P_{m,n+1} \\ P_{t,n+1} \end{bmatrix} - \alpha\begin{bmatrix} P_{m,n} \\ P_{t,n} \end{bmatrix}\right) -$$

$$\left(\begin{bmatrix} M_{mm} & M_{mt} \\ M_{tm} & M_{tt} \end{bmatrix}\begin{bmatrix} A_{m,n} \\ A_{t,n} \end{bmatrix} + \begin{bmatrix} C_{mm} & C_{mt} \\ C_{tm} & C_{tt} \end{bmatrix}\begin{bmatrix} V_{m,n} \\ V_{t,n} \end{bmatrix} + \right.$$

$$\left.\begin{bmatrix} K_{mm} & K_{mt} \\ K_{tm} & K_{tt}^0 \end{bmatrix}\begin{bmatrix} X_{m,n} \\ X_{t,n} \end{bmatrix}\right) - \left((1+\alpha)\begin{bmatrix} 0 \\ F_{t,n+1} \end{bmatrix} - \right.$$

$$\left.\begin{bmatrix} 0 & 0 \\ 0 & K_{tt}^1 \end{bmatrix}\begin{bmatrix} 0 \\ X_{t,n+1}^* \end{bmatrix} - \alpha\left(\begin{bmatrix} 0 \\ F_{t,n} \end{bmatrix} - \begin{bmatrix} 0 & 0 \\ 0 & K_{tt}^1 \end{bmatrix}\begin{bmatrix} 0 \\ X_{t,n}^* \end{bmatrix}\right)\right) +$$

$$\begin{bmatrix} M_{mm} & M_{mt} \\ M_{tm} & M_{tt} \end{bmatrix}\left(\frac{1}{\beta \Delta t}V_n + \frac{1}{2\beta}A_n\right) -$$

$$(1+\alpha)\begin{bmatrix} C_{mm} & C_{mt} \\ C_{tm} & C_{tt} \end{bmatrix}\left(\Delta t\left(1 - \frac{\gamma}{2\beta}\right)A_n - \frac{\gamma}{\beta}V_n\right)$$

denotes a dynamic load vector; and $$X_{n+1}^* = X_n + \Delta t V_n + \frac{\Delta t^2}{2}(1 - 2\beta)A_n \tag{3}$$

7. The vibration test system for structures according to claim 1, wherein:

the computer further comprises an experiment preparing means including an auxiliary vibratory displacement producing means, a linear stiffness calculating means, and a linear stiffness storing means;

the auxiliary vibratory displacement producing means produces an auxiliary vibratory displacement so that a displacement will occur along axes signified by degrees of freedom but no displacement will occur along the other axes;

the command signal producing means produces a command signal on the basis of the auxiliary vibratory displacement;

the linear stiffness calculating means calculates a linear stiffness on the basis of the load value measured by the load measuring means and the auxiliary vibratory displacement; and the linear stiffness storing means preserves the linear stiffness calculated by the linear stiffness calculating means so that the command displacement calculating means can use the linear stiffness.

8. The vibration test system for structures according to claim 1, wherein:

the computer further comprises a linear stiffness matrix calculating means for calculating a linear stiffness matrix that represents the real model portion, a degree-of-freedom degenerating means, and a linear stiffness storing means;

the linear stiffness matrix calculating means references a database relevant to the real model portion so as to calculate a detailed linear stiffness matrix representing the real model portion;

the degree-of-freedom degenerating means uses the linear stiffness matrix to calculate a degenerated linear stiffness matrix that represents a vibrating system with degrees of freedom required for a test; and the linear stiffness storing means preserves the degenerated linear stiffness matrix, which is calculated by the degree-of-freedom degenerating means, so that the command displacement calculating means can use the degenerated linear stiffness matrix.

9. A vibration test method for structures in which a vibration exciting means vibrates a real model portion that is a portion of a structure to be assessed, a load measuring means measures a load to be imposed on the real model portion by the vibration exciting means, and a computer receives a numerical model that represents a numerical model portion of the structure to be assessed other than the real model portion, also receives a load value measured by the load measuring means, and produces a command signal, which is transmitted to the vibration exciting means, according to the received numerical model and load value, wherein:

a command displacement calculating means calculates a displacement, which is made by the real model portion in a predetermined time after completion of measurement by the load measuring means, according to the load value measured by the load measuring means and an external force value;

a command signal producing means produces a command signal, which is transmitted to the vibration exciting means, using as a target value the displacement calculated by the command displacement calculating means; and a step control means controls the vibration exciting means, load measuring means, command displacement calculating means, and command signal producing means so that they will act cyclically, wherein:

for calculation of the displacement made by the real model portion, the command displacement calculating means uses an αOS method to for time integration to solve a vibrational equation that provides a displacement; and an equilibrium equation is solved based on an increment of the solution of the vibrational equation obtained at each time step from the solution thereof obtained at the previous time step.

10. The vibration test method for structures according to claim 9, wherein the command displacement calculating means uses the following formulae (14) and (3) and their definitions to calculate a displacement:

$$K_{n+1} * \Delta X_n = F_{n+1}^* \quad \text{where} \tag{14}$$

$$K_{n+1}^* = \left(\frac{1}{\beta \Delta t^2}\begin{bmatrix} M_{mm} & M_{mt} \\ M_{tm} & M_{tt} \end{bmatrix}\right. +$$

$$\left.(1+\alpha)\frac{\gamma}{\beta \Delta t}\begin{bmatrix} C_{mm} & C_{mt} \\ C_{tm} & C_{tt} \end{bmatrix} + (1+\alpha)\begin{bmatrix} K_{mm} & K_{tm} \\ K_{tm} & K_{tt}^0 \end{bmatrix}\right)$$

denotes a coefficient matrix, $$\Delta\begin{bmatrix} X_{m,n} \\ X_{t,n} \end{bmatrix}$$

denotes an unknown incremental displacement, and $$F_{n+1}^* = \left((1+\alpha)\begin{bmatrix} P_{m,n+1} \\ P_{t,n+1} \end{bmatrix} - \alpha\begin{bmatrix} P_{m,n} \\ P_{t,n} \end{bmatrix}\right) -$$

$$\left(\begin{bmatrix} M_{mm} & M_{mt} \\ M_{tm} & M_{tt} \end{bmatrix}\begin{bmatrix} A_{m,n} \\ A_{t,n} \end{bmatrix} + \begin{bmatrix} C_{mm} & C_{mt} \\ C_{tm} & C_{tt} \end{bmatrix}\begin{bmatrix} V_{m,n} \\ V_{t,n} \end{bmatrix}\right) +$$

-continued $$\begin{bmatrix} K_{mm} & K_{mt} \\ K_{tm} & K_{tt}^0 \end{bmatrix}\begin{bmatrix} X_{m,n} \\ X_{t,n} \end{bmatrix}\right) - \left((1+\alpha)\begin{bmatrix} 0 \\ F_{t,n+1} \end{bmatrix} -$$

$$\begin{bmatrix} 0 & 0 \\ 0 & K_{tt}^1 \end{bmatrix}\begin{bmatrix} 0 \\ X_{t,n+1}^* \end{bmatrix} - \alpha\left(\begin{bmatrix} 0 \\ F_{t,n} \end{bmatrix} - \begin{bmatrix} 0 & 0 \\ 0 & K_{tt}^1 \end{bmatrix}\begin{bmatrix} 0 \\ X_{t,n}^* \end{bmatrix}\right) +$$

$$\begin{bmatrix} M_{mm} & M_{mt} \\ M_{tm} & M_{tt} \end{bmatrix}\left(\frac{1}{\beta \Delta t}V_n + \frac{1}{2\beta}A_n\right) -$$

$$(1+\alpha)\begin{bmatrix} C_{mm} & C_{mt} \\ C_{tm} & C_{tt} \end{bmatrix}\left(\Delta t\left(1 - \frac{\gamma}{2\beta}\right)A_n - \frac{\gamma}{\beta}V_n\right)$$

denotes a dynamic load vector;

$$X_{n+1}^* = X_n + \Delta t V_n + \frac{\Delta t^2}{2}(1-2\beta)A_n \tag{3}$$

11. A program allowing a computer, which receives a load value measured by vibrating a real model portion that is a portion of a structure to be assessed and also receives a numerical model that represents a numerical model portion of the structure to be assessed other than the real model portion, to act as:

a command displacement calculating means for calculating a displacement, which is made by the real model portion in a predetermined time after completion of measurement by a load measuring means, according to the load value and a predefined external force value, for using an αOS method for time integration to solve a vibrational equation that provides a displacement, and for solving an equilibrium equation on the basis of an increment of the solution of the vibrational equation obtained at each time step from the solution thereof obtained at the previous time step;

a command signal producing means for producing a command signal, which is transmitted to the vibration exciting means, using as a target value the displacement calculated by the command displacement calculating means; and a step control means for controlling the vibration exciting means, load calculating means, command displacement calculating means, and command signal producing means so that they will act cyclically.

* * * * *